United States Patent [19]

Peterson

[11] 4,201,873

[45] May 6, 1980

[54] 9-DEOXY-9,10-DIDEHYDRO-PGD₂ ANALOGS

[75] Inventor: David C. Peterson, Portage, Mich.

[73] Assignee: The Upjohn Company, Kalamazoo, Mich.

[21] Appl. No.: 614,244

[22] Filed: Sep. 17, 1975

[51] Int. Cl.² .......................................... C07C 177/00
[52] U.S. Cl. .................................................. 562/503
[58] Field of Search ....... 260/468 D, 514 D, 514 CA; 562/503

[56] References Cited

U.S. PATENT DOCUMENTS 3,954,844  5/1976  Colton et al. ...................... 260/488

*Primary Examiner*—Robert Gerstl
*Attorney, Agent, or Firm*—Robert A. Armitage

[57] ABSTRACT

Prostaglandin analogs with the following cyclopentane ring structure:

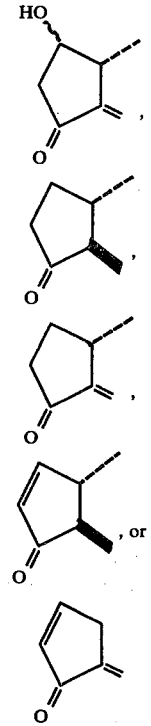

are disclosed along with intermediates useful in their preparation and processes for their preparation. These analogs are useful for some of the same pharmacological purposes as the prostaglandins, particularly and especially as blood platelet aggregation inhibitors.

1 Claim, No Drawings

9-DEOXY-9,10-DIDEHYDRO-PGD$_2$ ANALOGS

The present invention relates to 9-deoxy-9-didehydro-PGD$_2$, the essential material constituting a disclosure thereof, including its preparation and use, is incorporated here by reference from U.S. Pat. No. 4,016,184, issued Apr. 5, 1977.

I claim:

1. 9-Deoxy-9,10-didehydro-PGD$_2$.

* * * * *